United States Patent [19]

Mason et al.

[11] Patent Number: 4,790,990

[45] Date of Patent: Dec. 13, 1988

[54] MAMMALIAN LIVESTOCK FEED, MAMMALIAN LIVESTOCK FEED ADDITIVE, AND METHODS FOR USING SAME

[75] Inventors: J. Russell Mason, Philadelphia; Morley R. Kare, Narberth, both of Pa.; Dorf A. DeRovira, Branchburg, N.J.

[73] Assignee: Monell Chemistry Senses Center, Philadelphia, Pa.

[21] Appl. No.: 892,188

[22] Filed: Jul. 31, 1986

Related U.S. Application Data

[62] Division of Ser. No. 644,544, Aug. 27, 1984, abandoned.

[51] Int. Cl.$^4$ .................... A23K 1/18; A61K 31/24; A01N 37/18
[52] U.S. Cl. .................................. 424/438; 424/488; 424/493; 514/535; 514/918
[58] Field of Search .................. 424/438, 488, 493; 514/535, 918

[56] References Cited

U.S. PATENT DOCUMENTS

| | | | |
|---|---|---|---|
| 2,876,160 | 3/1959 | Schoch et al. | 167/82 |
| 2,967,128 | 1/1961 | Kare | 167/46 |
| 3,455,838 | 7/1969 | Marotta et al. | 252/316 |
| 4,344,857 | 8/1982 | Shasha et al. | 252/316 |
| 4,412,984 | 11/1983 | von der Loo et al. | 424/58 |
| 4,521,541 | 6/1985 | Rutherford et al. | 521/79 |

OTHER PUBLICATIONS

Palmer, T. K. "Pest Bird Damage Control in Cattle Feedlots: The Integrated Systems Approach", *Proc. Vertebr. Pest Conf.*, Monterey, Calif., 7:17–21, 1976.
Glahn, J. F., "Blackbird and Starling Depredations at Tennessee Livestock Farms", *Proc. Ninth Bird Control Seminar*, Bowling Green, Ohio.
Feare, C. J., and Swannack, K. P., "Starling Damage and Its Prevention at an Open-Fronted Calf Yard", *Anim. Prod.*, 26:259–265, (1978).
Glahn, J. F., and Otis, D. L., "Factors Influencing the Distribution of Bird Depredations at Livestock Feeding Areas in Tennessee", *Bird Damage Research Report No. 231*, Denver Wildlife Research Center, Denver, Colo., (1982).
Gough, P. M., and Beyer, J. W., "Bird-Vectored Diseases", *Proc. Fifth Great Plains Wildlife Damage Control Workshop*, (R. M. Timm and R. J. Johnson, Eds.), University of Nebraska, Lincoln, Neb., pp. 260–272, (1982).
Pilchard, E. J., "Experimental Transmission of Transmissible Gastroenteritis Virus by Starlings", *J. Vet. Res.*, 26(114): 1177–1179, (1965).
Besser, J. F., Royall, W. C., and Degrazio, J. W., "Baiting Starlings with DRC-1339 at a Cattle Feedlot", *J. Wildl. Manage.*, 31:48–51, (1967).
Besser, J. F., DeGrazio, J. W., and Guarino, J. L., "Costs of Wintering Starlings and Red-Winged Blackbirds at Feedlots", *J. Wildl. Manage.*, 32:179–180, (1968).

(List continued on next page.)

*Primary Examiner*—Fredrick E. Waddell
*Attorney, Agent, or Firm*—Woodcock Washburn Kurtz Mackiewicz & Norris

[57] ABSTRACT

The present application discloses a novel mammalian livestock feed additive containing a selective avian taste aversive agent, preferably dimethyl anthranilate, which is at least partially entrapped in an edible solid vehicle to improve its taste persistency. In the preferred embodiment, the edible vehicle is a modified food starch which is spray dried with the avian taste aversive agent. The disclosed livestock feed additive may be incorporated in a livestock feed to reduce the amount of feed lost to avian species, and to reduce the likelihood that mammals will be infected by avian transmitted diseases such as transmissible gastroenteritis. Alternatively, a mammalian poison is disclosed comprising an avian taste aversive additive which will increase the amount of that poison available for ingestion by mammalian target species and decrease the likelihood of secondary poisoning of a number of endangered species. An improved avian poison is also disclosed comprising a mixture of a discrete avian toxicant and a discrete avian food component, comprising an avian taste aversive additive which is at least partially entrapped in a vehicle to improve its taste persistency.

31 Claims, 4 Drawing Sheets

OTHER PUBLICATIONS

Feare, C. J., "Cost of Starling Damage of an Intensive Husbandry Unit", *Proc. British Insecticide and Fungicide Conf.*, 8:253-259, (1975).

Stickley, A. R., "Extended Use of Starlicide in Reducing Bird Damage in Southeastern Feedlots", *Proc. Bird. Cont. Sem.*, 8:79-89, (1979).

Twedt, D. J. and Glahn, J. F., "Reducing Starling Depredations at Livestock Feeding Operations Through Changes in Management Practices", *Proc. Verbebr. Pest. Conf.*, 10:159-163, (1982).

Feare, C. J. and Wadsworth, J. T., "Starling Damage on Farms Using the Complete Diet System of Feeding Diary Cows", *Anim. Prod.*, 32:179-183, (1981).

Bogadich, V., "The Use of Live Traps to Remove Starlings and Protect Agricultural Products", *Proc. Vertebr. Pest. Conf.*, 3:98-99, (1968).

West, R. R., Besser, J. F., and DeGrazio, J. W., "Starling Control in Livestock Feeding Areas", *Proc. Vertebr. Pest. Conf.*, 3:89-93, (1967).

Cunningham, D. J., Schafer, E. W., and McConnell, L. K., "DRC-1339 and DRC-2698 Residues in Starlings: Preliminary Evaluation of Their Effects on Secondary Hazard Potential", *Proc. Bird. Contr. Sem.*, 8:31-37, (1979).

Glahn, J. F., "Use of Starlicide to Reduce Starling Damage at Livestock Feeding Operations", *Proc. Great Plains Wildl. Dam. Wrkshp.*, 5:273-277, (1981).

Welty, J. C., "The Life of Birds", W. B. Saunders Book Co., Philadelphia, Pa., at p. 72, (1975).

Balcomb, R., "Secondary Poisoning of Red Shouldered Hawks with Carbonfuran", *J. Wildl. Manage.*, 47(4);1089-1132, (1983).

Kare, M. R., "The Special Senses", pp. 406-446, in P. D. Sturkie, ed., *Avian Physiology*, Cornell University Press, Ithica, N.Y., 776 pp., (1965).

Rogers, J. G., "Responses of Cages Red-Winged Blackbirds to Two Types of Repellents", *J. Wildl. Manage.*, 38:418-423, (1974).

Yang, R. S. H. and Kare, M. R., "Taste Response of a Bird to Constituents of Arthropod Defense Secretions", *Ann. Entomol. Soc. Am.*, 61:781-782, (1968).

Rogers, J. G., "Repellents to Protect Crops from Vertebrate Pests: Some Considerations for Their Use and Development", pp. 150-165, (R. W. Bullard, Ed.), *Flavor Chemistry of Animal Foods*, American Chemistry Society Press: Washington, D.C., 175 pp., (1978).

Reidinger, R. F. and Mason, J. R., "Exploitable Characteristics of Neophobia and Food Aversions for Improvements in Rodent and Bird Control", pp. 20-39, in D. E. Kaukikenen, ed., *Vertebrate Pest Control and Management: 4th Symposium.*, American Society for Testing and Materials, Philadelphia, Pa., (1983).

Kostelc, J. G., et al., "Quantitative Differences in Volatiles from Healthy Mouths and Mouths with Periodontitis", *Clinical Chemistry*, 27:842-845, (1981).

Bailey, E. P., "Abundance and Activity of Starling in Winter in Northern Utah", *Condor*, 68:152-162, (1966).

Morley R. Kare & Herbert L. Pick, Jr., "The Influence of the Sense of Taste on Feed and Fluid Consumption", *The Sense of Taste*, pp. 697-706.

MAMMALIAN LIVESTOCK FEED, MAMMALIAN LIVESTOCK FEED ADDITIVE, AND METHODS FOR USING SAME

This is a division, of application Ser. No. 644,544, filed 8/27/84, now abandoned.

BACKGROUND OF THE INVENTION

The present invention relates to the fields of livestock feeds, mammalian poisons and avian poisons, including in particular such feeds and poisons which include effective amounts of materials which are distasteful to avian species.

Certain embodiments of the present invention relate to materials and methods for reducing agricultural losses due to certain avian species, such as starlings. The cost of starlings to an individual farmer from consuming livestock feed can vary considerably from-negligible loss up to several thousand dollars during the fall-winter damage season. Palmer, T. K. 1976, "Pest Bird Damage Control in Cattle Feedlots: The Integrated Systems Approach", *Proc. Vertebr. Pest Control Conf.*, Monterey, Calif. 7:17-21. Generally, the large beef cattle feedlots of the west have the most significant losses. However, moderately sized dairy farms in Tennessee feeding 100 to several hundred head of cattle have been estimated to sustain losses of several hundred dollars during a 3-month damage season. Glahn, J. F., "Blackbird and Starling Depredations at Tennessee Livestock Farms", *Proc. Ninth Bird Control Seminar*, Bowling Green, Ohio. In Press. Although starlings can be a problem at hog operations, hog producers need not suffer significant feed loss problems with the use and proper adjustment of flip-top feeders and confinement of swine when feeding. In terms of percent feed loss farmers in Tennessee sustained up to 10% loss to birds of the grain component fed to livestock. A similar study in the United Kingdom estimated losses to farmers at up to 12%. Feare, C. J., and K. P. Swannack, "Starling Damage and its Prevention at an Open-Fronted Calf Yard", *Anim. Prod.* 26:259-265 (1978). Uses of repellents to reduce damage in actual field conditions for protecting costly ($8-12 per hundred weight) high protein feeds from starlings would probably be beneficial if costs of the repellent were below 10% the cost of the feed. This estimate considers only the limited data now available on the maximum cost due to feed loss only. It does not consider other factors such as potential for disease transmission.

The distribution and magnitude of feed loss damage on a national scale has not been studied. However, one study in the winter of 1980 inspected 287 livestock farms in 6 selected livestock producing countries in Tennessee. Glahn, J. F. supra. (In press). Results of this study indicated that 26% of the farms had more than a negligible damage problem including 6% with significant problems where losses exceeding $100 per season would be expected. Based on Tennessee Ag Statistics there were 43,000 hog and dairy farms in Tennessee in 1980. However, since the bird damage survey only sampled farms with greater than 20 head of livestock, the authors estimated the sampled population at 25,900 farms. Therefore, the 6% of the farms that could have benefitted from control measures was 1,554. These data are subject to seasonal changes in bird populations, weather conditions, and farm practices, but gives some idea of the number of farms that might benefit from bird control measures.

Further analysis of the previous data indicated that the primary factors influencing the distribution of damage was the proximity of roosting starlings to the farm, snow cover and mean temperatures below freezing on the day of inspection, and the number of head of livestock on feed. Glahn, J. F., and D. L. Otis, "Factors Influencing the Distribution of Bird Depredations at Livestock Feeding Areas in Tennessee", Bird Damage Research Report No. 231, Denver Wildlife Research Center, Denver, Colo. (1982). Since starlings winter throughout much of the United States, varying degrees of damage at farms is expected depending on winter weather conditions and size of livestock farms, with the most problems occurring at large operations in the northern wintering range of the starling. Although the total number of livestock farms in the U.S. is not readily available, in 1982 Tennessee had 85,000 dairy farms and 23,000 hog farms with 217,000 milk cows and 750,000 hogs compared with national livestock figures of 11 million milk cows and 53 million swine, respectively. The number of beef cattle on feed was not readily available nor was the number of major beef cattle feedlots.

It is extremely difficult to quantify the costs associated in the spread of disease to livestock by starlings essentially because it is difficult to document avian transmission in the first place. Two studies have implicated starlings with spread of transmissible gastroenteritis (TGE) to swine, but no known data exists for other livestock diseases. Gough, P. M., and J. W. Beyer, 1982, "Bird-Vectored Diseases", *Proc. Fifth Great Plains Wildlife Damage Control Workshop* (R. M. Timm and R. J. Johnson, Eds.), University of Nebraska, Lincoln, Nebr. pp. 260-272; and Pilchard, E. J. 1965, "Experimental Transmission of Transmissible Gastroenteritis Virus by Starlings", *J. Vet. Res.* 26(114):1177-1179. The costs of TGE may be substantial. For example, during the winter of 1978-79 a TGE outbreak occurring in southeast Nebraska resulted in over 10,000 pigs being lost in one county alone. Because of the possible threat of disease outbreak due to birds, livestock operators and particularly hog producers would be willing to use a material which would keep the birds out of their lots. Whether a feed repellent can do this depends both on the effectiveness of the material and the percent of the feed available to birds that would be treated.

Few objective estimates are available, but in addition to losses from starlings (*Sturnus vulgaris*), depredation from blackbird (i.e., grackle *Quicalus quiscula*, red-winged blackbirds *Agelaius phoeniceus*, and cowbird *Molothrus ater*) at swine and cattle feedlots is considered a serious economic problem. Besser, J. F. W. C. Royall and J. W. Degrazio, "Baiting Starlings with DRC-1339 at a Cattle Feedlot", *J. Wildl. Manage.*, 31:48-51 (1967); Besser, J. F. J. W. DeGrazio and J. L. Guarino, "Costs of Wintering Starlings and Red-Winged Blackbirds at Feedlots", *J. Wildl. Manage.* 32:179-180 (1968); Feare, C. J., "Cost of Starling Damage of an Intensive Husbandry Unit", *Proc. British Insecticide and Fungicide Conf.* 8:253-259 (1975); Feare, C. J. (1980), "The Economies of Starling Damage", *Econ. of Dam.* 2:39-54; Stickley, A. R., "Extended Use of Starlicide in Reducing Bird Damage in Southeastern Feedlots", *Proc. Bird. Cont. Sem.* 8:79-89 (1979); and Twedt, D. J. and J. F. Glahn, "Reducing Starling Depredations at Livestock Feeding Operations Through Changes in Management Practices", *Proc. Vertebr. Pest. Conf.* 10:159-163 (1982).

Losses may result from feed contamination and disease transmission, or from feed consumption, and problems are exacerbated when complete diets are presented in open troughs to which birds have access. See Russell, H. G., "Blackbird Control at Two Army Installations: Environmental Impact Statement", Office Chief Eng., Directorate Facilities Eng., Washington, D.C. (1975); Twedt D. J. and J. F. Glahn supra. (1982) and Rickaby, C. D., "A Review of the Nutritional Aspects of Complete Diets for Dairy Cows", *ADAS Q. Rev.*, 29:51–76 (1978). In that situation, up to 9% of the high protein fraction of the diet can be taken, thus depriving livestock of their high value nutrient source and altering the composition of the entire ration. Feare, C. J. and J. T. Wadsworth, "Starling Damage on Farms Using the Complete Diet System of Feeding Dairy Cows", *Anim. Prod.* 32:179–183 (1981). Efforts to control problem birds at feedlots mainly have involved trapping and/or the use of lethal chemical agents. See Besser, J. F., W. C. Royall and J. W. DeGrazio supra. (1967); Bogadich, V., "The Use of Live Traps to Remove Starlings and Protect Agricultural Products", *Proc. Vertebr. Pest. Conf.* 3:98–99 (1968); Levingston, P. E., "Winter Starling Control with DRC-1339." *Proc. Vertebr. Pest. Conf.* 3:100–103 (1967); West, R. R., J. F. Besser and J. W. DeGrazio., "Starling Control in Livestock Feeding Areas", *Proc. Vertebr. Pest. Conf.* 3:89–93 (1967); and Feare, C. J. and J. T. Wadsworth, supra. (1981). These approaches fail to create a sub-optimal environment for avian feeding activity, however, and the birds rapidly reinfest feedlots when control measures are relaxed. See Twedt, D. J. and J. F. Glahn, supra. (1982). Additional problems arise when lethal chemicals such as starlicide (1% C-chloro-p-toluidine hydrochloride on poultry pellets) are used, including primary and secondary hazards to non-target animals, development of bait aversion by target birds, and increased expense and labor in prebaiting, baiting and monitoring. See Cunningham, D. J., E. W. Schafer and L. K. McConnell, "DRC-1339 and DRC-2698 Residues in Starlings: Preliminary Evaluation of Their Effects on Secondary Hazard Potential", *Proc. Bird Contr. Sem.* 8:31–37 (1979); and Glahn, J. F., "Use of Starlicide to Reduce Starling Damage at Livestock Feeding Operations", *Proc. Great Plains Wildl. Dam. Wrkshp.* 5:273–277 (1981). Twedt and Glahn outlined management practices that could be implemented at feedlots to substantially reduce bird depredation. Twedt, D. J. and J. F. Glahn, supra. (1982) Among the suggested practices was the use of feeds that are either unpalatable or that cannot be metabolized by birds. In the latter case, relatively high levels of non-protein nitrogen (e.g., urea) and/or alfalfa might be added. In the former case, certain tastants might be used. Compounds do exist that are unpalatable to birds but readily accepted by mammals. See Welty, J. C., "The Life of Birds", W. B. Saunders Book Co., Philadelphia, Pa., at page 72 (1975).

One compound unpalatable to avian species is dimethyl anthranilate (DMA), non-toxic food flavoring approved for human consumption, but offensive to birds, even when presented at low concentrations. DMA has been suggested as a compound to reduce consumption of normally preferred foods by birds. See U.S. Pat. No. 2,967,128 (Kare). The Kare patent also discloses that certain compounds, particularly esters of anthranilic acid, esters of phenylacetic acid and dimethyl benzyl carbonyl acetate, are organic compounds which may be used to treat bird edibles in solution, suspension, emulsion or "other type of formulation". The most effective of the compounds disclosed in this patent is dimethyl anthranilate (methyl ortho-N-methylamino benzoate). Although U.S. Pat. No. 2,967,128 discloses that dimethyl anthranilate "has very excellent repellent action for prolonged periods and very small concentrations", subsequent testing has found that, when used outdoors, dimethyl anthranilate quickly loses its efficacy (see FIG. 1 of this application). Applicants hereto have theorized that the rapid loss of persistency under field conditions may result in part from photochemical decomposition of the dimethyl anthranilate to degradation products which exhibit little or no taste activity, and/or to the simple evaporation of those materials. Accordingly dimethyl anthranilate has not been widely used commercially since its discovery about a quarter of a century ago.

In addition to the problems encountered in preventing loss of mammalian livestock feeds to avian species, other problems stem from the unwanted ingestion of materials intended for consumption by mammalian species. For example, rodenticides and insecticides are often consumed by avian species. If they are not killed, they may concentrate lethal agents in such quantities as to cause the secondary poisoning of their predators. Since many of these predators are endangered species, a method of preventing avian prey from ingesting such substances should reduce the incidence of secondary poisonings. See Balcomb, R., "Secondary Poisoning of Red Shouldered Hawks With Carbonfuran", *J. Wildl. Manage.* 47(4);1089–1132 (1983).

In another context, it is often desired to poison and kill certain avian species, such as starlings. Presently, complete starlicides are available which comprise discrete poison and food components. In theory, starlings will, in the process of eating the presented food, consume a lethal amount of the presented poisons. Unfortunately, some starlings can effectively distinguish between the poisoned and unadulterated food, such that they avoid consuming lethal amounts of former. Accordingly, a need exists for an improved complete avian poison, such as a complete starlicide, which does not suffer fro these drawbacks.

SUMMARY OF THE INVENTION

The present application discloses a novel mammalian feed additive containing a selective avian taste aversive agent, preferably dimethyl anthranilate, which is at least partially entrapped in an edible solid vehicle to improve its taste persistency. In the preferred embodiment, the edible vehicle is a modified food starch (or dextrin) which is spray dried with the avian taste aversive agent. The disclosed feed additive may be incorporated in a livestock feed to reduce the amount of feed lost to avian species, and to reduce the likelihood that mammals will be infected by avian transmitted diseases such as transmissible gastroenteritis.

Alternatively, the present invention provides a mammalian poison comprising an avian taste aversive additive which will increase the amount of that poison available for ingestion by mammalian target species and decrease the likelihood of secondary poisoning of a number of endangered species.

An improved avian poison is also disclosed comprising a mixture of discrete avian toxicant, and an avian food component comprising an avian taste aversive additive which is at least partially entrapped in a vehicle to improve its taste persistency.

More particularly, the disclosed avian taste aversive agent may be selected from the group consisting of dimethyl anthranilate, esters of anthranilic acid, and the anthrilate derivatives which are disclosed in U.S. Pat. No. 2,967,128 (Kare) which is hereby incorporated by reference. The edible solid vehicle within which the taste aversive agent is at least partially entrapped should be a film forming material, a plasticizing agent, or a material which microencapsulates the avian taste aversive agent. Suitable materials include gelatin, gum arabic, food starch, malto dextrin, lactose, dextrin, corn syrup solids, the materials disclosed in U.S. Pat. No. 3,455,838 (which is hereby incorporated by reference), and mixtures thereof.

In accordance with the preferred embodiment of the present invention, the avian taste aversive agent comprises 1 to 60, preferably 5–50, more preferably 15–22 weight percent of said additive. This agent should be uniformly dispersed within the additive, the additive preferably being provided in dry powder form. The additive may be pelletized or otherwise mixed with a food component to form, for example, a mammalian livestock feed. When incorporated in a feed, said avian taste aversive agent should comprise 0.1 to 5, preferably 0.4 to 1.6, more preferably about 1 weight percent of the livestock feed.

Accordingly, a method is disclosed for reducing the amount of mammalian livestock feed lost to an avian species, comprising the steps of providing a selective avian taste aversive agent; producing a feed additive by at least partially entrapping said agent in an edible solid vehicle to extend its taste persistency; and incorporating said feed additive in said livestock feed in amounts sufficient to at least significantly reduce the amount of feed consumed by avian species. While spray drying is the preferred method of entrapping said agent within the matrix of a solid vehicle, extrusion, drum drying, fluidized bed drying and microencapsulation are other suitable techniques.

By providing the aforementioned livestock feed, methods are facilitated for reducing the incidence of avian transmitted disease in mammalian livestock populations. Furthermore, the disclosed avian taste aversive additive facilitates the provision of an improved mammalian poison exhibiting reduced consumption by non-target species.

Accordingly, a primary object of the present invention is the provision of an improved mammalian feed additive which is not palatable to common avian species, such as starlings and blackbirds.

A further object of the present invention is the provision of an improved mammalian livestock feed comprising such additiees.

A further object of the present invention is the provision of improved methods for reducing the amount of mammalian livestock feed lost to avian species.

A further aim of the present invention is the provision of a method for reducing the incidence of avian transmitted disease such as transmissible gastroenteritis, in mammalian livestock populations.

Another object of the present invention is the provision of improved mammalian and avian poisons.

These and other objects of the present invention will become apparent from the following more detailed description.

BRIEF DESCRIPTION OF THE DRAWINGS

FIG. 3(A) represents the mean consumption of food incorporating a spray dried DMA-starch additive by deprived (squares) or satiated (circles) groups of starlings in 1-hour, 1-choice tests; FIG. 3(B) is a graph of mean consumption in grams of food comprising a DMA spray dried starch additive by deprived (solid or open squares) or satiated (solid or open circles) groups of starlings in 1-hour, 1-choice tests. Closed squares and circles represent consumption of plain food. Open squares and circles represent DMA containing samples. For both panels (A, B), vertical capped bars represents standard errors of the means;

DESCRIPTION OF THE PREFERRED EMBODIMENTS

Figure 1:
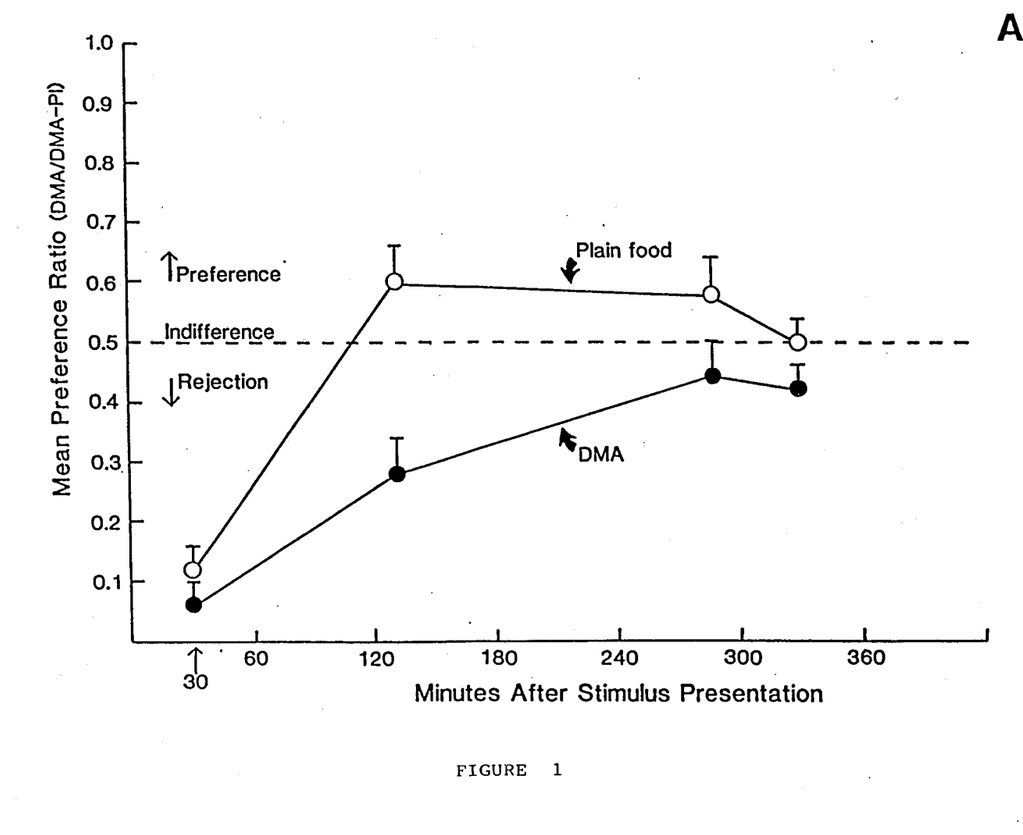
FIG. 1 is a graph of the mean preference ratio of starlings consuming untreated sunflower seeds (plain food) vs. such seeds immediately after treatment with an aqueous emulsion of DMA (1 to 1000 parts in distilled water), showing the relative lack of persistance of DMA over a six hour period.
Figure 2:
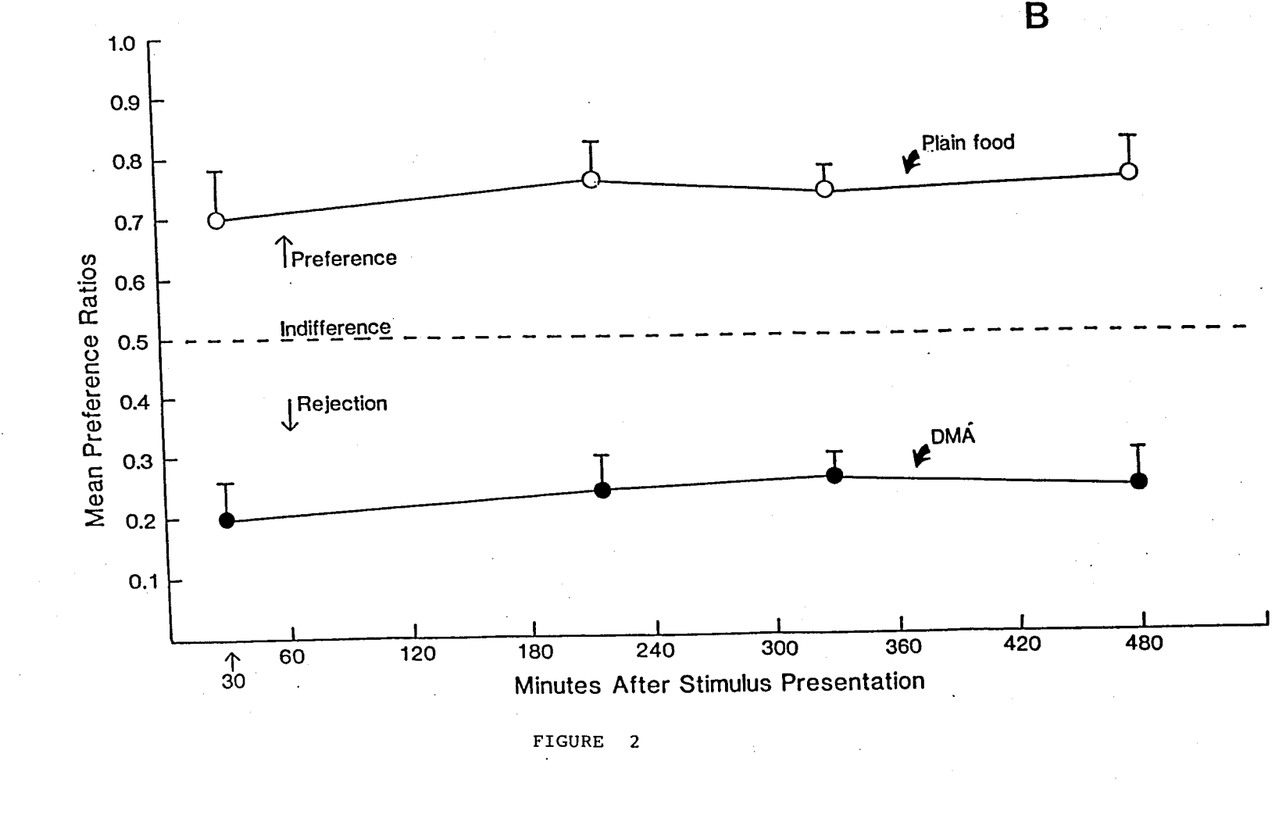
FIG. 2 is a graph of mean preference similar to FIG. 1 wherein the seeds were treated with the liquids propylene glycol, and DMA in propylene glycol, showing some improved persistency over an eight hour period.

Tests performed by the applicants have shown that DMA, sprayed as a simple aqueous emulsion sprayed on food lacks sufficient taste persistency to serve as an economically attractive taste aversive agent. FIG. 1 is a graph of the mean preference ratio of starlings consuming untreated sunflower seeds (identified as plain food) versus such seeds shortly after treatment with an aqueous emulsion of DMA (1:1000 parts in distilled water). As seen from FIG. 1, the achieved negative preference with DMA quickly approaches indifference over periods as short as 5 to 6 hours. As seen in FIG. 1, no significant differences exist after 300 minutes post to-presentation between the DMA and plain food samples of FIG. 1. It is theorized that the use an aqueous emulsion to apply DMA may increase its tendency to "flash off", thereby minimizing its taste persistency. FIG. 2 reflects a similar preference rejection test wherein DMA is applied in another liquid (propylene glycol) vehicle. As seen in FIG. 2, there is some improved taste persistency when propylene glycol, as opposed to water, is used as the vehicle. Nonetheless, it is believed that, once the evaporation of the propylene glycol is complete, the effectiveness of DMA will rapidly decrease. In any event, liquids such as propylene glycol are difficult to handle, and in a typical treatment situation would probably have to be made up fresh on an almost daily basis to produce consistent results.

DMA is light sensitive and will degrade to a non-effective form in light without adequate protection. Also, as DMA has a certain volatility, the compound will evaporate over a period of time unless precautions are taken to retard this evaporation. This is why a liquid which is plated or sprayed (absorbed) onto a substrate is less effective over longer terms. DMA as is commonly available in the marketplace is a fairly costly ingredient (16-29.00/lb). Because of the necessity to keep within the guidelines of the cost of effective percentage use, the percentage fix (DMA in substrate) needs, in some instances, to be kept as high as possible. The utilization of DMA as a repellent to birds, as used in pig or cattle feeds, are two examples of usages which have all three of the above outlined inherent problems: (a) need for light protection, (b) need for dispersion of effective ingredient, while minimizing evaporation of the ingredient, (c) need to increase fix in order to minimize effective cost in use.

In accordance with the preferred embodiment of the present invention, it is preferred to at least partially entrap an avian taste aversive agent in an edible solid vehicle to improve its taste persistency.

DMA may be protected from light degradation by entrapping and/or drying the DMA within, for example, an opaque matrix. Examples of this would include, for example, the microencapsulation, extrusion, fluidized bed drying, drum drying, spray drying or any other acceptable liquid in solid entrapment technique. Microencapsulation may be performed in accordance with U.S. Pat. No. 3,455,838, which has been incorporated by reference. Another example, which also aids in the product's dispersibility in use, is spray drying. Typically the oil to be entrapped within the matrix to be sprayed dried may, for example, be as little as 5% approaching as much as 55%, with percentage fixes or applications of oil to dry matrix most commonly falling within the 15 to 22% range. The matrices effective for this include film formers such as: gelatin, gum arabic, or certain modified food starches, as well as plasticizing agents such as: malto dextrin, lactose, dextrin, or corn syrup solids, and combinations of any or all of these, or other suitable ingredients. In the case where the higher fixes (30%) are desired, a combination of one or more of gum arabic, dextrin or modified food starch needs to be used in order to maximize protection against light and volatilization at these higher levels by virtue of their ability to entrap the DMA at those levels.

Under normal circumstances, the opaque matrix will normally be sufficient to protect DMA from photochemical degradation. If desired, the DMA may further be protected by incorporating an ultraviolet blocking agent in or as part of the vehicle. One such blocking agent is a blocking resin available from National Starch and Chemical Corporation as No. 28-3307. This blocking agent may be dispersed in a DMA/resin blend in DMA:resin ratios of between 1:1 and 1:25, preferably about 1:14. If desired, the DMA/resin blend may be dispersed in a pH adjusted aqueous substrate or in a solvent system, such as ethyl acetate. This substrate/solvent system may be employed or treated so that the solvent is evaporated to leave the DMA:resin mix. It should be noted that the resultant DMA:resin combination is suitable for subsequent entrapment in an edible solid vehicle, but itself does not exhibit the required taste persistency to act as a suitable mammalian feed additive in accordance with the present invention.

Examples of effectively dried products are as follows:

| Ex. 1 | Fluid Bed Procedure - | |
|---|---|---|
| | ECD-61 (Waxy Maize) | 50.00 |
| | DMA | 50.00 |
| | | 100.00 |

The above was tried at 25% to 75% fix of DMA to ECD-61. The higher ranges indicated a poor entrapment. Optimization of maximum fix percentage versus retention was indicated around 30-60%.

| Ex. 2 | Spray Drying - Examples of suitable conditions for drying are as follows: Niro Spray Dryer | |
|---|---|---|
| | Outlet Temp. | 90° C. to 105° C. |
| | Inlet Temp. | 180° C. to 205° C. |

The following are examples of suitable spray dried formulae:

| Water | 225 parts | | 150 parts |
|---|---|---|---|
| Nadex 772 (dextrin) | 150 parts | Capsul Spray Starch | 150 parts |
| DMA | 150 parts | | 150 parts |
| | 525 parts | | 450 parts |

In both cases, the water is removed in the drying process, resulting in a yield of a dry powder. The above are only examples of optimum entrapment. Other blends can be used.

Accordingly, it will be seen that the preferred mammalian feed additive comprises a selective avian taste aversive agent which comprises 1-60, preferably 5-50, more preferably about 15-22 weight percent of said additive. This agent is uniformly dispersed with the additive, which is preferably in dry powder form.

Experience has indicated that materials and agents to which birds exhibit a taste aversion may not maintain sufficient persistency or effectiveness to be commercially viable when used in field conditions. Accordingly, a series of laboratory experiments was conducted, followed by actual field trials, in order to determine the effectiveness of the mammalian feed additives and feed in accordance with the present invention. The results of these laboratory experiments are set forth as follows.

LABORATORY EXPERIMENT 1

METHODS

Sixty adult starlings were decoy-trapped at Sundusky, Ohio. The birds were brought to the laboratory and housed 3 to a cage (dimensions $75 \times 75 \times 40$ cm) under a 10/14 light-dark cycle in a room with an ambient temperature of $23 \pm 2°$ C. Each group was visually isolated with pieces of cardboard ($75 \times 40$ cm). Water was always available and, before the experiment began, the birds were permitted free access to Purina Flight Bird Conditioner (PFBC) in food hoppers attached to the front of each cage.

STIMULI

Six concentrations of DMA (w/w) in food were prepared by mixing 1 kg of PFBC with various quantities o lipophyllic starch containing 20% DMA, prepared by spray drying as described above. Plain lipophyllic starch was also added to each food sample, so that all contained 80 g of starch. The DMA concentrations were (a) 0.0% [i.e., 80 g plain starch, 1 kg PFBC]; (b) 0.4% [i.e., 20 g DMA starch, 60 g plain starch, 1 kg PFBC]; (c) 0.6%; (d) 0.8%; (e) 1.0%; and (f) 1.6%. The same batches of treated food were used for the duration of the experiment, and each batch was stored in a covered plastic tub at room temperature ($23 \pm 2°$ C.).

REPELLENCY TESTS

The birds (n=3/cage) were assigned to four groups (n=5 cages/group). Then, the various DMA concentrations were presented to each group under four conditions. These conditions were: (a) one-choice test, 14 hrs food deprived; (b) one-choice test, no feed deprivation; (c) two-choice, 14 hrs food deprived; and (d) two-choice test, no food deprivation. Among groups, the sequence of test situations was completely counterbalanced. Testing occurred during the first hour of light (0800-0900 hrs), 6 days/week, for 4 consecutive weeks. Food deprivation (i.e., removing the food bins from the front of the cages) occurred between dark onset of one day (1800 hrs), and light onset of the next (0800 hrs).

For the one-choice tests, food was removed from the cages of the birds that had not been food deprived, and then all groups were given 50 g of one of the six DMA concentration (A-F) in a standard food cup (7.5 cm diam.). The food cups were presented in plastic tubs ($28 \times 18 \times 12$ cm), so that spillage could be collected and assessed. All birds were tested once with each concentration, and the order of presentation of the different mixtures was counterbalanced, so that 5 (1/cage) of the 6 mixtures were presented daily to each group. After one hour, the tubs were removed, and consumption and spillage were measured.

For the 2-choice tests, food was removed from the cages of the birds that had not been food deprived, and then all groups were given 2 covered food cups, each containing 50 g of food. The cups were presented in plastic tubs that had been divided into 2 equal sections by a cardboard insert (2 cm high). This permitted collection of spillage from each cup. One food cup in each tub contained 50 g of one of the six DMA mixtures (0.0-1.6%). The other cup in every case contained 50 g of mixture 0.0% (PFBC mixed with plain starch). Presentation of the 6 stimulus combinations was completely counterbalanced, such that 5 of the 6 stimulus combinations were presented daily. Each cage within each group received the combinations in a different order. In addition, the relative position of the 2 food cups presented each day was randomized to control for the possibility of position learning of DMA-containing samples by the birds. As in the 1-choice tests, the tubs were removed from the cages after one hour, and consumption and spillage from each food cup were assessed.

A 2-way analysis of variance (ANOVA) with repeated measures on both factors was used to assess consumption in 1-choice tests. One factor (2 levels) of this analysis was consumption of food when food deprived versus consumption when satiated. The other factor (6 levels) as consumption of food treated with each of the 6 concentrations of DMA. A 3-way ANOVA with repeated measures on all factors was used to assess consumption in 2-choice tests. The factors in this analysis were: (1) consumption when food deprived versus consumption when satiated (2 levels) (2) consumption of food across days (6 levels); (3) consumption of DMA-treated food versus plain food within trials (2 levels). Tukey b post-hoc comparisons (Winer, 1962, 1962:198) were used to isolate significant differences ($P<0.05$) among means. See Winer, B. J. 1962. *Statistical Princicles of Experimental Design* McGraw-Hill Book Co.: New York, N.Y., 907pp. Spillage was statistically assessed in the same fashion as consumption, but was not reported here because it simply reflected consumption.

LABORATORY EXPERIMENT 2

METHOD

Twenty starlings were randomly selected from the groups of birds used in Experiment 1. These birds were individually housed, visually isolated, and tested as described in Experiment 1. That is, the birds were assigned to 4 groups (n =5/group) and the repellency of DMA for each bird was tested in 1- and 2-choice tests under conditions of food deprivation or satiation. The concentrations of DMA presented during these tests were the same as those used in Experiment 1. Testing occurred during the first hour of light (0800-0900 hrs), 6 days a week (Monday through Saturday), for 4 weeks.

A 2-way ANOVA with repeated measures on both factors was used to assess the data from the 1-choice tests, and a 3-way ANOVA with repeated measures on all factors was used to assess the data from the 2- choice tests. The factors (and levels of factors) in these analyses were identical to those reported for use in Experiment 1. Tukey b post-hoc comparisons ($P<0.05$) were used to isolate significant differences ($P<0.05$) among means. Spillage data were assessed in the same fashion as consumption, but are not reported as they merely reflected consumption.

RESULTS

LABORATORY EXPERIMENT 1

In 1-choice tests, birds ate more after deprivation, regardless of the DMA concentration present in starch on the food ($F=6.9$; $df=1,228$; $P<0.009$). However, both food deprived and satiated birds exhibited clear differences in consumption as a function of the DMA concentration ($F=16.6$; $df=5,228$; $P<0.0001$). Tukey tests indicated that more was eaten of plain food than of any of the DMA-treated samples ($P<0.05$). Within DMA-treated samples, the most was eaten of the weakest concentration (0.4%) ($Ps<0.05$), and the least was eaten of the strongest concentration (1.6%) ($Ps<0.05$). There were no differences in consumption among the other DMA-treated samples ($P>0.10$) (FIG. 3A).

Figure 3:
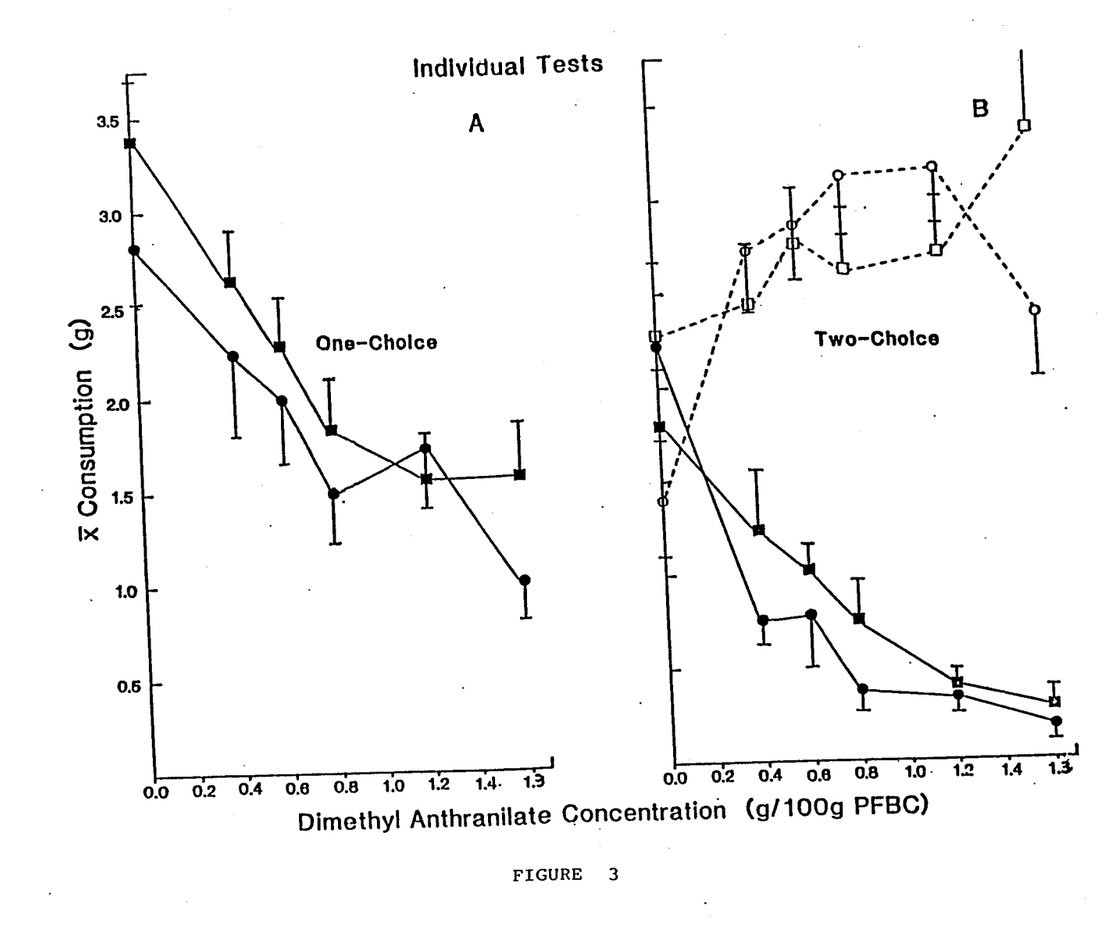
FIG. 3 is a side by side comparison of 1 choice (FIG. 3A) and 2 choice (FIG. 3B) consumption tests.

Thus, FIG. 3, illustrates the following: (A) Mean consumption (g) of DMA-treated food by deprived (■) or satiated (●) groups of starlings in 1-hour, 1-choice tests. (B) Mean consumption (g) of DMA-treated food by deprived (■,□) or satiated (●,o) groups of starlings in 1-hour, 1-choice tests. Closed squares and circles represent consumption of plain food. For both panels (A,B), vertical capped bars represent standard errors of the means.

In 2-choice tests, birds again ate more after 18 hrs of food deprivation, regardless of DMA concentration present on the food ($F=4.2$; $df=1,456$; $P<0.04$). However, within each test, plain food was reliably preferred to food treated with DMA ($F=291.3$; $df=1,456$; $P<0.00001$), and there were again differences in consumption, depending on the concentration of DMA presented ($F=7.4$; $df=5,456$; $P<0.00001$). Tukey tests indicated that within DMA-treated samples, the most was eaten of 0.4% ($Ps<0.05$), and the least was eaten of samples containing high DMA concentrations (1.2% and 1.6%), respectively; ($Ps<0.05$). There were no differences in consumption among the other DMA-treated samples ($P>0.10$) (FIG. 3B).

RESULTS

LABORATORY EXPERIMENT 2

In 1-choice tests, there were no significant differences between consumption when food deprived versus satiated birds were compared (P>0.06). However, there were significant differences in consumption depending on the concentration of DMA presented (F=9.2; df=5,228; P<0.0001). Tukey tests indicated that the most was eaten of untreated food (0.0%, P<0.05) and least was eaten of food containing 1.6% DMA (P<0.05). Among the other treated samples, less was eaten of 0.8% and 1.2% DMA than of 0.4% and 0.6% DMA (Ps <0.05, respectively; FIG. 4A).

In 2-choice tests, there were significant differences in consumption depending on the concentration of DMA presented (F=13.5; df=5,456; P<0.00001), and within tests, plain food (0.0% was reliably preferred to treated food (F=246.5; df=5,456; P<0.00001). However, because the 3-way interaction among: (a) consumption when food deprived or satiated; (b) consumption of plain versus treated food; and (c) consumption of food treated with different concentrations of DMA was significant (F=2.4; df=5,456; P<0.04), we interpreted the analysis in terms of that higher order effect. Tukey tests indicated that the birds ate more when food deprived (P<0.05), but that overall consumption in 2-choice tests depended on the concentration of DMA presented (Ps<0.05). The higher the concentration of DMA present, the less was eaten of either DMA-treated or plain food (FIG. 4B).

Figure 4:
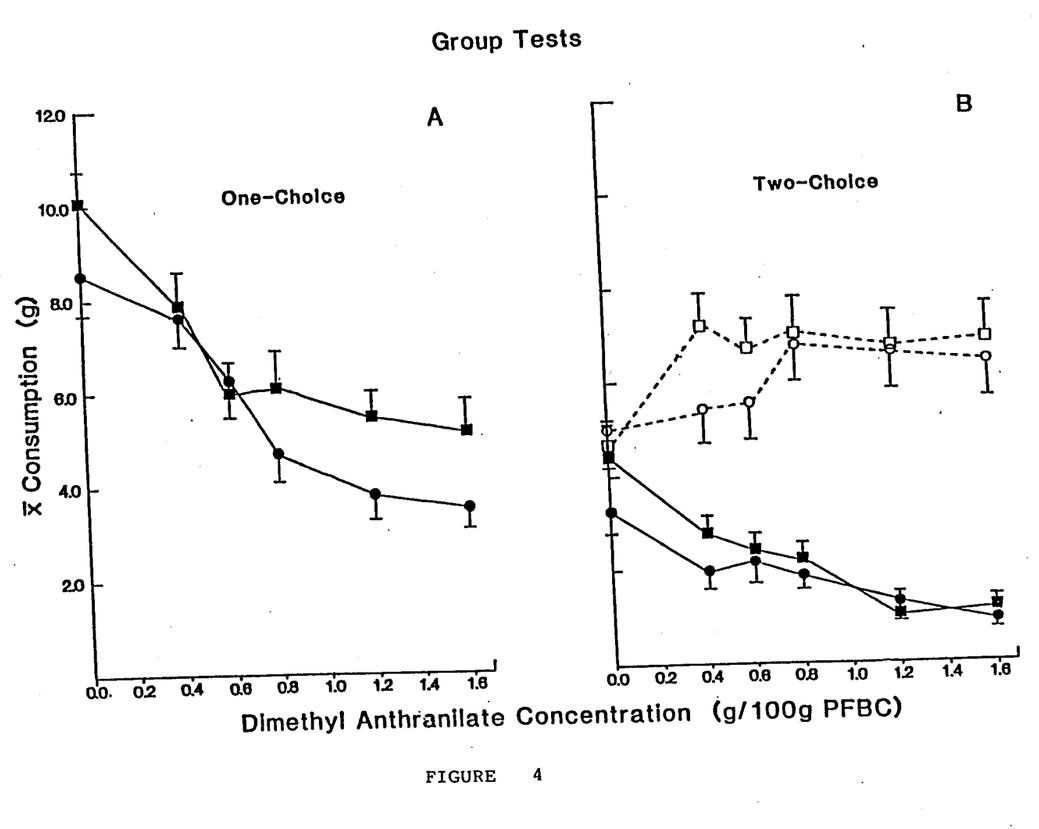
FIG. 4 is a graph similar to FIG. 3 representing the results of group tests, the meanings of the notations being the same as that described above in connection with FIG. 3.

Thus, FIG. 4 illustrates the following: (A) Mean consumption (g) of DMA-treated food by food-deprived (■) or satiated (•) individual starlings in 1-hour, 1-choice tests. (B) Mean consumption (g) of DMA-treated food by deprived (■,□) or satiated (•,o) individual starlings in 1-hour, 2-choice tests. Closed squares and circles represent consumption of treated foods. Open squares and circles represent consumption of plain food. For both panels (A,B), vertical capped bars represent standard errors of the means.

DISCUSSION AND MANAGEMENT IMPLICATIONS OF LABORATORY TESTS

In the above described laboratory experiments, DMA in a spray dried starch vehicle used as a food additive was shown to effectively repel both groups of birds and individuals in 1and 2-choice tests, and when food deprived and satiated. Repellency was concentration-dependent and long-lasting, and even after repeated experiences, the birds continued to exhibit strong rejection of the DMA containing feed. Such durability was especially striking, given that at the end of individual tests, the birds had been exposed to DMA in food 6 days per week for 4 weeks. Similar concentrations of DMA are not rejected by mammals in feeding tests, and in some cases, preferences for the DMA containing feed are observed.

Consumption of DMA-treated food was consistently higher for groups of birds than for individuals, and for food deprived than for satiated birds. Even so, relatively low concentrations of DM significantly reduced consumption. For example, 1.6% of DMA reduced consumption (relative to consumption of 0.0% treated food) in 1-choice tests by 40% and 54%, respectively, for groups of birds and individuals that had been food deprived. Similar but more dramatic reductions in consumption were observed in 2-choice tests. Because DMA is offensive to a wide variety of birds besides starlings, including Japanese quail (*Coturnix japonica*), pigeons (*Columba livia*), red-winged blackbirds (*Agelaius phoeniceus*), jungle fowl (*Gallus gallus*) and herring gulls (*Larus argentatus*) the usefulness of the compound as a bird repellent was expected to be general. Kare, M. R., "The Special Senses", Pages 406-446. in P. D. Sturkie, ed., *Avian Physiology*, Cornell University Press, Ithaca, N.Y., 766 pp. (1965); Rogers, J. G., "Responses of Cages Red-Winged Blackbirds to Two Types of Repellents", *J. Wildl. Manage.* 38:418-423 (1974); and Yang, R. S. H. and M. R. Kare, "Taste Response of a Bird to Constituents of Arthropod Defense Secretions", *Ann. Entomol. Soc. Am.* 61:781-782 (1968).

Based on the above-described laboratory data, it was postulated that the DMA containing additive and food products might prove useful for bird control in some feedlot settings. First, use of the compound would result in a less optimal food source, without primary or secondary hazards to non-target animals. Second, because starlings do not become accustomed to the taste of the compound, reduction in damage is likely to be long-lasting. Third, because the chemical would be incorporated directly in the feed, learned aversions by target birds to animal feed, feeding troughs, etc., would enhance the efficacy of DMA, and not serve as a drawback as it does for toxicants that are applied to bait materials separate from feed. Fourth, DMA sprayed dried starch is relatively inexpensive, even when produced in small test quantities. Concentrations as high as 1.6% (the highest concentration used here) would only cost about $2.00/50 lb. bag. Substantial reductions in cost would occur if DMA sprayed dried starch were produced in large quantities, and/or if less expensive procedures (e.g., plating DMA on starch) were substituted for spray drying. Costs for pre-baiting and monitoring would be eliminated.

Of course, it was not suggested that DMA was likely to act as an absolute repellent in all feedlot situations, with all avian pests. As suggested by Rogers differences in the materials to be protected from damage often influence the efficacy of control compounds. See Rogers, J. G., "Repellents to Protect Crops From Vertebrate Pests: Some Considerations for Their Use and Development", Pages 150-165, (R. W. Bullard, Ed.) *Flavor Chemistry of Animal Foods.* American Chemical Society Press: Washington D.C. 175pp. (1978). Preferred foods, for example, may be harder to protect, and the relative palatability of alternative foods may influence the repellency of DMA-treated foods. The nature of the pest species may also be important. As such, DMA may be most effective with omnivorous birds such as starlings or pigeons that use both taste and vision for food selection. See Reidinger, R. F. and J. R. Mason, "Exploitable Characteristics of Neophobia and Food Aversions for Improvements in Rodent and Bird Control", Pages 20-39, in D. E. Kaukienen, ed., *Vertebrate Pest Control and Management Materials: 4th Symposium.* American Society for Testing and Materials, Philadelphia, Pa. (1983). Accordingly, field tests were designed to address these and other questions.

FIELD TESTS

Materials and Methods

Study Areas—Four livestock farms were selected in southcentral Kentucky for use as test sites. To achieve independence with regard to bird populations, these sites were geographically spaced minimum of 9.5 km apart with 2 sites in Warren and 2 sites in Barren County. Starling barn roosts occurred at 3 of the 4 testsites (sites 1, 3, 4) and all sites were within the foraging range of 1+million blackbird/starling roosts in Franklin and Munfordville, Ky.

Site #1 was a hog lot within the boundary of the Western Kentucky University Farm located in Warren County, approximately 6.4 km south of Bowling Green, Ky. at the junction of U.S. 31 W and Elrod Road. At this site, 6 pens of feeder pigs were fed a corn/soybean meal hog developer via flip-top self-feeders. Spillage, as well as malfunctioning lids on some feeders, provided birds with a constant food source.

Site #2 was the Bill Balance farm located in Warren County, 21 km northeast of Bowling Green, Ky. on Highway US 31 W. This was a Holstein heifer feeding operation where 50–60 head of dairy cattle were fed corn silage supplemented with a ground corn mixture. Silage was normally offered to cattle twice a day with some silage available to the cattle and the birds throughout the day.

Site #3 was the G. W. Bellamy hog and cattle farm, located in Barren County 6.4 km south of Park City, Ky. on KY Highway 225 at the Cumberland Parkway. At this site, hogs and beef cattle (Angus and Hereford steers) were fed a ground corn/soybean ration from self-feeders within a single fenced lot. Feed was available to livestock and birds throughout the day.

Site #4 was the Jimmy Gardner hog farm, located in Barren County on KY Highway 90, 11.3 km northwest of Glasgow. This site was the outside the facility of a major swine feeding operation where most of hogs were fed in confinement. It consisted of a fenced pasture containing 2 barns with a number of flip-top self-feeders that provided a ground corn/soybean hog developer ration to a varying number of feeders pigs and breeding stock.

Test and Control Feeds—Feed was prepared by Ralston Purina Co., St. Louis, Mo. Both test and control samples were pelletized, and contained 40% alfalfa, soy, corn, and meat meal protein, 19% non-protein nitrogen (urea), 5.5% calcium, and 1% phosporous. Test samples also contained DMA spray-dried on lipophyllic starch at a concentration approximating 0.8% (w/w). The actual concentration, as determined by gas chromatography was 0.6%. Kostelc, J. G. et al, "Quantitative Differences in Volatiles from Healthy Mouths and Mouths with Periodontitis" *Clinical Chemistry* 27:842–845, (1981)

Pilot work determined that the livestock pellets as supplied were too large ($2.0 \pm 0.01$ cm long $\times 0.6 \pm 0.01$ diam) to compete favorably (for bird depredation) with feed exposed for livestock.

For that reason, feed samples were taken to a roller mill in Bowling Green, Ky., and crushed (crushed Particles size: $0.45 \pm 0.04$ cm long $0.36 \pm 0.02$ cm diam).

Procedure

Pre-baiting—On 1/22/84, V-shaped 2.5 m long $\times 0.6$ m wide $\times 0.4$ m deep roofed wooden troughs were placed at each site. Over the next 10 days (1/23/84–2/1/84), 10 kg of poultry crumbles were exposed in each every 48 hrs. Samples were retrieved, and consumption (to the nearest gram) was recorded for each 2 day periods, except between 1/30/84–2/1/84, when rain dissolved the crumbles.

Pre-treatment—Between 2/2/84 and 2/5/84 (r days), 5 kg of control feed was exposed daily between 0650 and 0830, at each site. Consumption was measured to the nearest gram for each 8 hr period. This pre-treatment period served to establish a baseline for consumption of the high protein feed.

Ambient temperature, weather conditions (i.e., cloud and snow cover, precipitation), and the number and species of birds present at each site and on or near the experimental troughs, were visually estimated, and recorded daily when feed was exposed (0650–0830) and when it was retrieved (1450–1630).

Treatment 1—Sites #1 and #3 were selected randomly, and on 2/6/84 and 2/7/84, 5 kg of test feed was exposed at each between 0650 and 1630 hrs. Control feed was exposed at sites #2 and #4. On 2/8/84, 10 kg of poultry crumbles was exposed at each site for 8 hours, as a rest period. On 2/9/84 and 2/10/84, treatment conditions were reversed and test feed was exposed at sites #2 and #4. This second treatment period was followed by a second rest day, on which poultry pellets (not crumbles) were exposed. On 2/12/84, poultry crumbles treated with DMA starch were exposed for 8 hours at sites #1 and #3, while untreated poultry crumbles were exposed at sites #2 and #4. Treatment conditions were reversed the on 2/13/84 and DMA treated crumbles were exposed at sites #2 and #4. On all treatment and rest days, temperature, weather conditions, bird pressure, and consumption were recorded Treatment 2

To gain additional data on consumption of DMA treated poultry crumbles, another 7 day treatment period was carried out between 2/27/84–3/4/84. During the first 3 days of the trial (2/27/84–2/29/84), 5 kg of DMA treated crumbles were exposed at sites #1 and #3 for 8 hours, while control crumbles (treated with lipophyllic starch alone) were exposed at sites #2 and #4. On 3/1/84, 5 kg of untreated poultry pellets were exposed at each site. During the final 3 days of the trial (3/2/84–3/4/84), treatment conditions were reversed (i.e., DMA treated crumbles were exposed at sites #2 and #4). Consumption (to the nearest gram) was measured on each day. Temperature, weather, and bird pressure were not recorded during Treatment 2.

Analysis

Two-way analysis of variance (ANOVAs) with repeated measures on the second factors were used to assess changes in temperature. Days were the independent variable in one analysis, while sites was the independent variable in the other. Time (a.m. vs. p.m.) was the repeated factor in both analyses. Two-way ANOVAs with repeated measures on the second factors were also used to assess bird pressure. The independent and repeated variables in these analyses were identical to those used for analyses of temperature. Species abundance was assessed by a two-way ANOVA with repeated measures on the second factor. The independent variable in this analysis was species while the repeated variable was feedlots.

Pre-baiting and pre-treatment consumption was assessed in a one-way repeated measures ANOVA. The factor in this analysis was daily consumption. In order to obtain estimates of daily consumption for the pre-baiting period, the amount consumed during each 48 hr measurement period was halved.

Consumption during treatment periods 1 and 2 was assessed separately in two two-way ANOVAs with repeated measures on both factors. The variables in these analyses were (a) order of exposure (i.e., first presentation of DMA and control feed at each site, second presentation of each feed at each site, third presentation of each feed at each site), and (b) DMA vs. control food. Tukey b post-hoc tests were used to isolate significant differences among means. Winer, B. J., *Statistical Principles of Experimental Design* McGraw-Hill Book Co.: New York, N.Y. 907pp (1962). In addition, Spearman rank-order correlation coefficients were calculated between bird numbers (and species diversity), and temperature, % cloud cover, % snow cover, and snow depth.

RESULTS

Weather Conditions

Temperature fluctuated significantly during the course of the trial (F $(11,36) = 36.1$, $p < 0.01$), and between morning and afternoon (F$(1,36) = 38.3$, $p < 0.001$), although on any given day, there were no differences among lots ($p > 0.25$). Temperatures range from $-17°$ to $+22°$ C. with a mean daily temperature of $+7.4 \pm 1.8°$ C. Cloud and snow cover varied from 0 to 100%, and precipitation varied from 0% to heavy rain or snow. The weather conditions are summarized in TABLE I:

TABLE 1

WEATHER CONDITIONS DURING PRE-TREATMENT AND TREATMENT. MEANS ($\pm$Sn) ARE PRESENTED FOR TEMPERATURE, % CLOUD COVER, % SNOW COVER, AND SNOW DEPTH.
PRE-TREATMENT PERIOD (2/2-2/5)

| Days | Temperature a.m. | Temperature p.m. | Cloud Cover (%) | Precip Type | Snow Cover (%) | Snow Depth |
|---|---|---|---|---|---|---|
| 1 | 9.7 ± 2.6 | 12.3 ± 1.0 | 0 ± 0.0 | | 0 ± 0.0 | 0 ± 0.0 |
| 2 | 7.2 ± 0.3 | 10.9 ± 1.3 | 100 ± 0.0 | Rain | 0 ± 0.0 | 0 ± 0.0 |
| 3 | 2.6 ± 0.6 | 8.0 ± 0.5 | 30 ± 7.8 | | 0 ± 0.0 | 0 ± 0.0 |
| 4 | −1.1 ± 0.5 | −8.2 ± 1.0 | 100 ± 0.0 | Snow | 100 ± 0.0 | 2.6 ± 1.2 |
| 1 | 10.0 ± 2.9 | −9.9 ± 1.0 | 0 ± 0.0 | | 100 ± 0.0 | 4.8 ± 0.7 |
| 2 | −17.0 ± 6.9 | 4.7 ± 6.5 | 0 ± 0.0 | | 100 ± 0.0 | 4.5 ± 1.0 |
| 3 | −10.2 ± 2.6 | 14.0 ± 5.7 | 0 ± 0.0 | | 8 ± 6.4 | 2.3 ± 0.3 |
| 4 | −2.2 ± 4.5 | 20.7 ± 3.0 | 0 ± 0.0 | | 68 ± 7.2 | 1.5 ± 0.2 |
| 5 | 8.5 ± 0.6 | 16.7 ± 2.5 | 94 ± 7.2 | Rain | 2.5 ± 2.9 | 0.5 ± 0.0 |
| 6 | 12.5 ± 2.9 | 20.2 ± 2.8 | 100 ± 0.0 | Rain | 0 ± 0.0 | 0 ± 0.0 |
| 7 | 22.5 ± 1.7 | 21.2 ± 2.2 | 22.2 ± 9 | | 0 ± 0.0 | 0 ± 0.0 |
| 8 | 13.1 ± 2.5 | 18.5 ± 2.5 | 92 ± 5.5 | Rain | 0 ± 0.0 | 0 ± 0.0 |

BIRD PRESSURE

Because data on bird pressure at feedlots and in the vicinity of experimental troughs were identical, only the results for bird pressure at feedlots are presented. There were significant differences among lots, and between morning and afternoon in the numbers of birds present (F$(3,40) = 14.5$, $p < 0.01$). There were also significant differences among lots and across days in the number of birds present (F$(33,44) = 4.6$, $p < 0.0$). Post-hoc analyses revealed that more birds were present during pre-treatment (1723.7 ±71.8) than treatment (996.2±55.9) ($p < 0.01$). While there were differences in the numbers of birds present at sites in the morning and afternoon, such differences were not consistent. At site #1, the number of birds reliably increased from morning (101.9±17.4) to afternoon (225.0±57.2) ($p < 0.05$). Conversely, at site #4, the number of birds decreased from morning (120.0±34.3) to afternoon (63.8±12.8) ($p < 0.05$). There were no differences between the numbers of birds present in the morning (59.4±11.3; 80.0±18.4) and the afternoon (79.5±28.6; 83.0±17.3) at feedlots #3 and #,, respectively ($p > 0.25$). Feedlot #1 had significantly greater numbers of birds (42.7±9.5) than the other sites (ps<0.01), while feedlot #2 had the fewest birds 0 (12.4±3.2) (ps<0.01). Feedlots #3 and #4 had intermediate numbers of birds (21.3±4.3; 23.4±5.8, respectively).

There were significant overall differences (F$(5,138) = 40.6$, $p < 0.001$), and differences among lots (F$(3,414) = 8.8$, $p < 0.05$) in the frequency with which species were observed. Also, there was significant interaction between lots and species abundance (F$(15,414) = 4.1$, $p < 0.01$). Starlings were always the most numerous ($p < 0.001$). Sparrows (Passer domesticus) were next most commonly observed ($p < 0.001$). Grackles, cowbirds, red-wings, mourning doves (*Zenaida macroura*), and feral pigeons (*Columba livia*) were also present. Species abundance was greater at site #1 than at the other sites ($p < 0.01$). These results are summarized in TABLE 2:

TABLE 2

MEAN NUMBERS (±Sn) AND PERCENTAGES OF SPECIES PRESENT AT FEEDLOTS DURING PRE-TREATMENT AND TREATMENT

| Species | Feedlots 1 | 2 | 3 | 4 |
|---|---|---|---|---|
| Starlings | 210.0 ± 43.2 (77%) | 69.4 ± 15.0 (82%) | 105.4 ± 17.0 (88%) | 118.5 ± 27.5 (85%) |
| Grackles | 16.7 ± 12.9 (6%) | 0.0 ± 0.0 (0%) | 2.1 ± 2.2 (2%) | 9.6 ± 5.3 (7%) |
| Cowbirds | 22.9 ± 11.9 (8%) | 2.1 ± 2.2 (3%) | 1.0 ± 1.1 (1%) | 0.4 ± 0.4 (0%) |
| Redwings | 2.1 ± 2.1 (1%) | 0.0 ± 0.0 (0%) | 0.0 ± 0.0 (0%) | 0.0 ± 0.0 (0%) |
| Sparrows | 18.3 ± 6.5 (7%) | 7.0 ± 3.5 (9%) | 19.4 ± 5.6 (15%) | 11.7 ± 4.6 (8%) |
| Doves | 2.1 ± 1.7 (1%) | 0.1 ± 0.1 (0%) | 0.0 ± 0.0 (0%) | 0.0 ± 0.0 (0%) |
| Overall | 42.7 ± 9.5 (100%) | 12.4 ± 3.2 (100%) | 21.3 ± 4.3 (100%) | 23.4 ± 5.8 (100%) |

The number of birds at each feedlot was inversely and significantly correlated with temperature ($r = = 0.74$, $p < 0.01$), and positively and significantly correlated with snow cover ($r = +0.54$, $p < 0.05$). There were no significant correlations between the number of birds present and % cloud cover ($r = -0.46$, $p > 0.10$) or snow depth ($r = +0.48$, $p > 0.10$). Also, thee where no significant correlations between the number of species present at feedlots and temperature ($r = -038$, $p > 0.25$), % snow cover ($r=0.32$, $p>0.25$), % cloud cover ($r=-0.08$, $p>0.50$, or snow depth ($r=0.23$, $p>0.25$).

CONSUMPTION

There was significant changes in consumption during pre-baiting and pre-treatment ($F(5,15)=15.2$, $p<0.001$). Post-hoc tests indicated that there was higher consumption of poultry crumbles than control livestock feed during pretreatment ($p<0.01$). See TABLE 3 as follows:

TABLE 3

MEAN CONSUMPTION ($\pm$Sn) OF POULTRY CRUMBLES DURING PRE-BAITING AND OF CONTROL LIVESTOCK FEED DURING PRETREATMENT

| Sites | Prebaiting (1/23-1/28) | Pretreatment (2/2-2/4) |
|---|---|---|
| 1 | 9.98 ± 0.02 kg | 0.54 ± 0.3 kg |
| 2 | 6.60 ± 2.56 kg | 0.53 ± 0.37 kg |
| 3 | 4.90 ± 2.97 kg | 0.60 ± 0.34 kg |
| 4 | 5.80 ± 1.29 kg | 0.50 ± 0.32 kg |

There were significant differences in consumption of test and control feed during Treatment 1 )$F(1,3)=33.6$, $p<0.001$). Post-hoc analyses indicated that there was significantly less consumption of test ($0.005\pm0.005$ kg) than control ($2.025\pm0.65$kg) feed on all days ($ps<0.001$). There was consumption of test ($0.9\pm0.3$ kg) and control ($2.6\pm0.8$) poultry crumbles ($p<0.001$), than of livestock feed, both these differences were not significant ($p>0.20$). See TABLE 4 as follows:

TABLE 4

CONSUMPTION OF TEST (DMA-TREATED) AND CONTROL FEEDS BY BIRDS DURING TREATMENT 1.

| | Days | | | | | | | |
|---|---|---|---|---|---|---|---|---|
| | Livestock Feed | | Rest | Livestock Feed | | Rest | Poultry Crumbles | |
| Feedlots | 2/6 | 2/7 | 2/8 | 2/9 | 2/10 | 2/11 | 2/12 | 2/13 |
| 1 | *0.04 | *0.0 | 5.0 | 1.0 | 0.8 | 1.3 | *0.6 | 4.6 |
| 2 | 1.3 | 1.3 | 4.7 | *0.0 | *0.0 | 0.6 | 1.5 | *1.6 |
| 3 | *0.0 | *0.0 | 2.3 | 0.9 | 0.6 | 0.7 | *0.8 | 2.4 |
| 4 | 2.1 | 2.7 | 4.3 | *0.0 | *0.0 | 0.5 | 2.0 | *1.6 |

*DMA-treated feed

Analysis of data collected during treatment 2 produced results similar to those of the earlier treatment period. Significantly less of the DMA-treated crumbles were consumed ($0.15\pm0.06$ kg) than of the control crumbles $2.68\pm0.32$) on all days ($F(1,3)=185.1$, $p<0.001$) (Table 5).

DISCUSSION OF FIELD TESTS

Bird depredation at all sites was related to weather conditions (i.e., the lower the temperature, and the greater the snow cover, the greater the numbers of depredating birds). This finding is consistent with previous work demonstrating the importance of weather to livestock feed depredations. Bailey, E. P., "Abundance and Activity of Starling in Winter in Northern Utah", *Condor* 68:152-162 (1966); and Stickley, A. R., supra. (1979). Consumption was recorded on all days, however, suggesting that at least some birds (e.g., barn-roosting starlings and sparrows) were using the feedlots as a consistent food source.

Starlings and sparrows were by far the most frequently observed bird species at all sites. This finding is also consistent with previous work, although in the present study, starlings appeared to be more of a problem at swine (sites #1, 3, 4) than cattle operations (site #2). Glahn, J. F., "Blackbird and Starling Depredations at Tennessee Livestock Farms", (in review) (1984); and Palmer, C. D., supra. (1976).

Regardless of weather conditions, or the numbers of birds or species present, DMA treated feed markedly reduced consumption of feed. This was true both on days when high protein livestock feed was exposed and on days when poultry crumbles were exposed. Consumption of treated feed did not increase over successive exposures, strongly suggesting that depredating birds do not habituate to its offensive properties.

Consumption of treated poultry crumbles was higher than consumption of treated livestock feed. No clear interpretation can be given to this effect, since the observed differences in effectiveness could reflect several factors. First, because the DMA did not bind well with the crumbles, it may have blown off, or settled to the bottoms of the troughs. Consistent with this possibility, observable amounts of DMA powder were present in the bottoms of troughs when food was removed. Alternatively, the aversiveness of the compound may decrease when it is merely present on the surface of food, and not present in the food matrix. Finally, the relative palatability of the feed may have interacted with the repellency of DMA. As suggest by Rogers, differences in materials to be protected from damage often influence the efficacy of control compounds. Rogers, J. G., supra. (1978). Preferred food, such as poultry crumbles, may be relatively harder to protect.

Overall, the present results demonstrate that DMA is useful as a feed additive to reduce bird depredation at livestock feedyards. Use of the compound appears to result in a less optimal food source without primary or secondary hazards to non-target animals. Because birds in the present study did not become accustomed to the compound, we speculate that reductions in damage would be long-lasting. Moreover, because the chemical is incorporated directly in the feed, learned aversions by target birds would enhance the efficacy of DMA, and not serve as a drawback as it does for toxicants that are applied to bait materials separate from feed. Finally, DMA produced in large quantities would be relatively inexpensive and costs for pre-baiting and monitoring would be eliminated.

TABLE 5

CONSUMPTION OF TEST (DMA-TREATED) AND CONTROL POULTRY CRUMBLES DURING TREATMENT 2.

| | Days | | | | | | |
|---|---|---|---|---|---|---|---|
| | Poultry Crumbles | | | Rest | Poultry Crumbles | | |
| Feedlots | 2/27 | 2/28 | 2/29 | 3/1 | 3/2 | 3/3 | 3/4 |
| 1 | *0.04 | *0.0 | *0.68 | 4.95 | 3.69 | 1.92 | 3.93 |
| 2 | 1.5 | 3.75 | 2.18 | 2.41 | *0.06 | *0.02 | *0.00 |
| 3 | *0.23 | *0.25 | *0.31 | 4.99 | 2.96 | 3.02 | 2.88 |
| 4 | 1.01 | 3.98 | 1.34 | 3.94 | *0.08 | *0.05 | *0.00 |

*DMA-treated poultry crumbles

We claim:

1. An improved mammalian feed additive, comprising a selective avian taste aversive agent selected from the group consisting of an ester of anthranilic acid a substituted anthranilic derivative and a mixture thereof, said agent being at least partially entrapped in an edible solid lipophilic starch vehicle to improve its taste persistency, said agent comprising 1 to 60 weight percent of said additive.

2. The additive of claim 1 wherein said selective aversive agent comprises dimethyl anthranilate.

3. The additive of claim 1 wherein said vehicle comprises modified food starch.

4. The additive of claim 1 wherein said agent is spray dried with said vehicle.

5. The additive of claim 1 wherein said vehicle is substantially opaque to ultraviolet light.

6. The additive of claim 1 wherein said agent is microencapsulated in said vehicle.

7. The additive of claim 1 wherein said agent comprises 5 to 50 wt. % of said additive.

8. The additive of claim 7 wherein said agent comprises 15 to 22 wt. % of said additive.

9. The additive of claim 1 wherein said agent is uniformly dispersed within said additive.

10. The additive of claim 1 in dry powder form.

11. The additive of claim 1 wherein said vehicle is a film forming material.

12. The additive of claim 1 wherein said vehicle is a plasticizing agent.

13. The additive of claim 1 wherein said vehicle is selected from the group consisting of a food starch, malto dextrin, dextrin, a corn syrup solid and a mixture thereof.

14. A mammalian livestock feed, comprising:

(a) a food component, and (b) an avian taste aversive additive, said additive comprising a selective avian taste aversant agent, said agent being selected from the group consisting of an ester of anthranilic acid, a substituted anthranilic derivative and a mixture thereof, said agent being at least partially entrapped in an edible lipophilic starch vehicle to improve its tast persistency, said agent comprising about 0.1 to 5 weight percent of said mammalian livestock feed.

15. The feed of claim 14 comprising 0.4 to 1.6 wt. % of said agent.

16. The feed of claim 14 comprising less than about 1 wt. % of said agent.

17. The feed of claim 16 wherein said agent is dimethyl anthranilate.

18. A method of reducing the amount of mammalian livestock feed lost to avian species, comprising the steps of:

(a) providing a selective avian taste aversant agent selected from the group consisting of an ester of anthranilic acid, substituted anthranilic derivative and a mixture thereof.

(b) producing a feed additive by at least partially entrapping said agent in an edible solid lipophilic starch vehicle to extend its taste persistency, whereby said agent comprises 1 to 60 weight percent of said additive;

(c) incorporation said feed additive in said livestock feed in amounts sufficient to at least significantly reduce the amount of feed consumed by avian species.

19. The method of claim 18 wherein step (a) comprises providing dimethyl anthranilate.

20. The method of claim 18 wherein step (b) comprises spray drying said agent with said vehicle.

21. The method of claim 18 wherein step (b) comprises spray drying dimethyl anthranilate in a starch.

22. The method of claim 18 wherein step (c) comprises forming feed pellets comprising said additive.

23. The method of claim 18 wherein steps (b) and (c) are performed to achieve the desired reduction of avian feed consumption over the normal mammalian feeding period.

24. The method of claim 18 wherein step (b) comprises dispersing said agent throughout said vehicle.

25. The method of claim 18 wherein step (b) comprises incorporating said agent in a vehicle which is opaque to ultraviolet light.

26. The method of claim 18 wherein step (b) comprises drying said agent within the matrix of a solid vehicle.

27. The method of claim 18 wherein step (b) comprises microencapsulating said agent within said vehicle.

28. The method of claim 18 wherein step (b) comprises extruding said vehicle with said agent.

29. The method of claim 18 wherein step (b) comprises drum drying said vehicle with said agent.

30. The method of claim 18 wherein step (b) comprises fluidized bed drying said vehicle with said agent.

31. A mammalian livestock feed comprising:

(a) a food component, and (b) an avian taste aversive additive, said additive comprising an avian taste aversive agent selected from the group consisting of an ester of anthranilic acid, a substituted anthranilic derivative and a mixture thereof, said agent having been at least partially encapsulated by spray drying in a lipophilic food starch to improve its taste persistency, said additive comprising 1 to 60 weight percent of said agent, and said feed comprising 0.1 to 5 weight percent of said agent.

* * * * *

UNITED STATES PATENT AND TRADEMARK OFFICE
CERTIFICATE OF CORRECTION

PATENT NO. : 4,790,990

DATED : December 13, 1988

INVENTOR(S) : Mason et al.

It is certified that error appears in the above-identified patent and that said Letters Patent is hereby corrected as shown below:

Title page: the name of the third inventor reading "Dorf. A. DeRovira" should be --Dolf A. DeRovira--. Page 1, the name of the Assignee reading "Monell Chemistry Senses Center" should be --Monell Chemical Senses Center--.

Column 4, line 43, "fro" should be --from--.

Column 8, line 59, "o" should be --of--.

Column 9, line 53, "as" should be --was--; line 64, "Princicles" should be --Principles--.

Column 11, line 62, "DM" should be --DMA--.

Column 13, line 2, following "spaced" should be an ----a--.

Column 16, line 28, "(82%)" should be --(88%)--, and "(88%)" should be --(82%)--; line 62, "r==0.74" should be --r=-0.74--; line 66, "thee where" should be --there where--; line 68, "038" should be --0.38--.

Column 17, line 5, "was" should be --were--; line 26, after "there was" should be inserted --higher--.

Column 18, line 61, after the word "acid" there should be inserted --,--; line 62, "anthranilic" should be --anthranilate--.

Column 19, lines 29-30, "anthranilic" should be --anthranilate--; line 32, "tast" should be --taste--; line 46, "anthranilic" should be --anthranilate--.

UNITED STATES PATENT AND TRADEMARK OFFICE
CERTIFICATE OF CORRECTION

PATENT NO. : 4,790,990

DATED : December 13, 1988

INVENTOR(S) : Mason et al.

It is certified that error appears in the above-identified patent and that said Letters Patent is hereby corrected as shown below:

Column 20, line 4, "incorporation" should be --incorporating--; line 42, "anthranilic" should be --anthranilate--.

Signed and Sealed this

Eighth Day of August, 1989

Attest:

DONALD J. QUIGG

*Attesting Officer*

*Commissioner of Patents and Trademarks*